United States Patent

Serrels et al.

[11] Patent Number: 5,625,156
[45] Date of Patent: Apr. 29, 1997

[54] APPARATUS FOR SENSING EXHAUST GAS

[75] Inventors: Dana M. Serrels, Davison; Brian M. Bibb, Ortonville; Stephen J. Myers, Owosso; John A. Horton, Clio; Walter Jenkins, Linden, all of Mich.

[73] Assignee: General Motors Corporation, Detroit, Mich.

[21] Appl. No.: 639,822

[22] Filed: Apr. 29, 1996

[51] Int. Cl.$^6$ .................................................. G01N 1/14
[52] U.S. Cl. ................................ 73/863.51; 73/863.81
[58] Field of Search .......................... 73/23.32, 863.41, 73/863.43, 863.51–863.58, 863.61, 863.81, 863.82, 863.85, 864.33, 864.81, 866.5

[56] References Cited

U.S. PATENT DOCUMENTS

| | | |
|---|---|---|
| 1,649,241 | 11/1927 | Lewis ............................ 73/863.51 |
| 1,967,428 | 7/1934 | Quereau ....................... 73/863.51 |
| 2,475,857 | 7/1949 | Reinert ......................... 73/863.51 |
| 3,625,065 | 12/1971 | Thompson ................... 73/863.51 |
| 3,745,983 | 7/1973 | Sweeney ...................... 123/119 R |
| 3,803,921 | 4/1974 | Dieterich ...................... 73/863.51 |
| 4,018,089 | 4/1977 | Dzula et al. .................. 73/863.61 |
| 4,148,211 | 4/1979 | Sawa et al. ................... 73/23 |
| 4,177,787 | 12/1979 | Hattori et al. ................ 123/198 |
| 4,534,213 | 8/1985 | Misikidani .................... 73/863.51 |
| 4,535,316 | 8/1985 | Wertheimer et al. ........ 388/34 |
| 4,658,790 | 4/1987 | Kitahara ........................ 123/440 |
| 4,763,628 | 8/1988 | Mieno et al. ................. 123/440 |
| 5,074,987 | 12/1991 | Thompson .................... 204/410 |
| 5,138,834 | 8/1992 | Maund et al. ................ 60/276 |
| 5,177,464 | 1/1993 | Hamburg ...................... 340/439 |
| 5,252,949 | 10/1993 | Kirby et al. .................. 340/632 |
| 5,265,417 | 11/1993 | Visser et al. .................. 60/274 |
| 5,357,750 | 10/1994 | Ito et al. ....................... 60/274 |
| 5,385,016 | 1/1995 | Zimlich et al. ............... 60/274 |
| 5,408,215 | 4/1995 | Hamburg ...................... 340/439 |
| 5,444,974 | 8/1995 | Beck et al. ................... 60/274 |
| 5,456,124 | 10/1995 | Colvin .......................... 73/863.11 |

*Primary Examiner*—Robert Raevis
*Attorney, Agent, or Firm*—Anthony Luke Simon

[57] ABSTRACT

An apparatus for sensing exhaust gas comprising: first and second tubular passages; a solid plug through which the first and second tubular passages pass and to which the tubular passages are sealingly engaged; a sampling chamber mounted to and in flow contact with the first and second tubular passages, wherein the first tubular passage provides gas flow into the sampling chamber and the second tubular passage takes gas flow out of the sampling chamber; and a flow passage having a tubular wall with an opening therein to which the solid plug is sealingly engaged, wherein the first and second tubular passages extend from inside the flow passage, through the plug, to the sampling chamber mounted outside of the flow passage.

2 Claims, 3 Drawing Sheets

APPARATUS FOR SENSING EXHAUST GAS

This invention relates to an apparatus for sensing exhaust gas.

BACKGROUND OF THE INVENTION

In a known manner, exhaust gas oxygen sensors are used in automotive exhaust management systems to monitor the performance of the engine and/or catalytic converter in controlling vehicle emissions. In some examples, the exhaust gas oxygen sensors are used as feedback for engine control.

In a typical system, the oxygen sensor is mounted in a catalytic converter or in an exhaust gas flow pipe such as a manifold pipe or post-converter flow pipe. The sensor body is mounted in the pipe or converter wall with the sensing area of the sensor extending into the exhaust gas flow stream within the pipe to sense the oxygen content thereof. In such systems, the body of the sensor projects out of the converter or pipe perpendicular to the flow axis of the converter or pipe. This configuration requires clearance, for example in the vehicle floor pan, for the sensor projecting out of the converter or pipe.

SUMMARY OF THE PRESENT INVENTION

It is an object of this invention to provide an apparatus for sensing exhaust gas according to claim 1.

Advantageously, this invention provides an apparatus for sensing exhaust gas that comprises a mounting structure for an oxygen sensor that minimizes the space radial from the center of a flow pipe or converter necessary for mounting the oxygen sensor.

Advantageously, this invention provides an apparatus for sensing exhaust gas that removes the oxygen sensor's sensing element from the direct flow stream of the exhaust gas.

Advantageously, this invention provides an apparatus for sensing exhaust gas that eliminates the necessity of mounting the oxygen sensor through the wall of the catalytic converter or exhaust flow pipe so that it is aligned perpendicular to the direction of exhaust gas flow.

Advantageously, according to a preferred example of this invention, an apparatus for sensing exhaust gas is provided comprising first and second tubular passages, a solid plug through which the two tubular passages pass and to which the tubular passages are sealingly engaged, a sampling chamber mounted to and in flow contact with the two tubular passages, wherein one of the tubular passages provides gas flow into the sampling chamber and the other tubular passage takes gas flow out of the sampling chamber; and a flow passage having a tubular wall with an opening therein to which the solid plug is sealingly engaged, wherein the first and second tubular passages extend from inside the flow passage, through the plug, to the sampling chamber mounted outside of the flow passage.

BRIEF DESCRIPTION OF THE DRAWINGS

The present invention will now be described by way of example with reference to the following drawings in which.

DETAILED DESCRIPTION OF THE INVENTION

Figure 1:
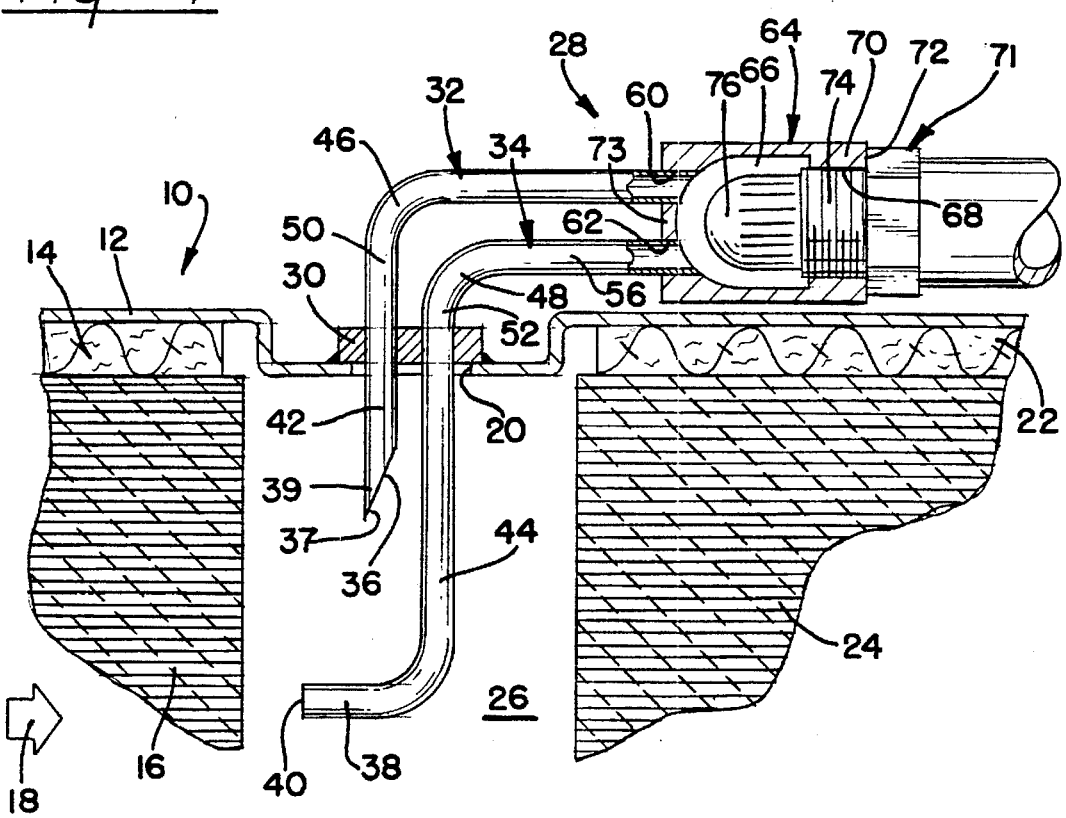
FIGS. 1 and 2 illustrates a first example according to this invention.
Figure 2:
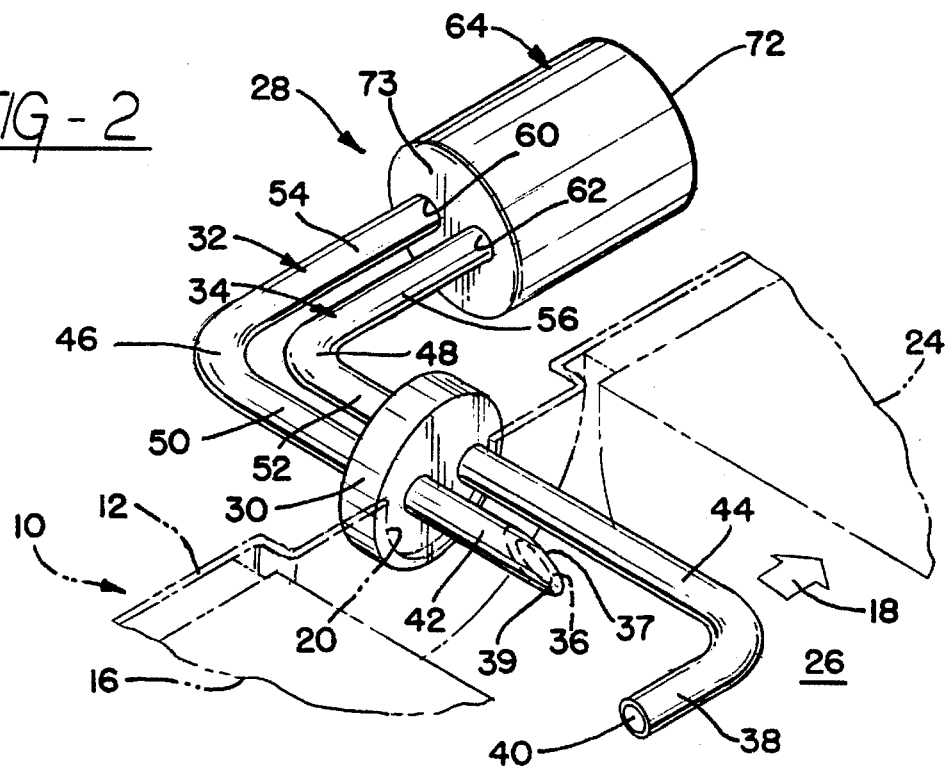

Referring now to FIGS. 1 and 2, a catalytic converter 10 is shown having an outer shell 12 comprising stainless steel and including therein first and second converter monoliths 16 and 24 of a known type. The monoliths 16 and 24 each contain a catalyst of a known type for reducing undesirable gas species from the exhaust gas flowing through the converter 10 in the direction of arrow 18. The monoliths 16 and 24 are retained in place by the monolith retention material 14 and 22 shown. The monolith retention material 14, 22, generally has an insulating property and operates to limit movement of the substrates 16 and 24 within the converter shell 12 and to evenly distribute, along the outer surface of the substrates 16 and 24, pressure retaining the substrates 16 and 24 in place. Preferred retention material 14, 22 consists of expandable ceramic/organic or intumescent mats or stainless steel mesh, depending on the material selected for construction of the substrates.

A hole 20 is pierced in the shell 12 between the first and second monoliths 16 and 24. The example apparatus 28 according to this invention is mounted to the catalytic converter 10 at hole 20.

The example apparatus 28 according to this invention includes first and second flow tubes 32 and 34, solid plug 30, for example, a short cylinder of steel, and housing 64 for the sampling chamber 66. The solid plug 30, flow tubes 32 and 34 and housing 64 for sampling chamber 66 may be assembled as a unit and mounted to the catalytic converter 10, for example, by welding solid plug 30 to the shell 12 sealing the opening 20. The weld is preferably around the entire interface between the plug 30 and the shell 12.

With the plug 30 welded to the shell 12, the flow tubes 32 and 34 each extend through the plug 30 into the flow passage 26. The tube 34 is a pitot tube having an end 38 axially parallel to the direction of flow 18 with inlet 40 facing into the flowing exhaust gas. The section 44 of the tube 34 extends within the passage 26 from the end 38 toward the plug 30, where the tube 34 passes through the plug 30, arising therefrom as section 52. Tube 34 then has a bend 48 of approximately 90 degrees leading to the exterior axially aligned section 56, which terminates in an opening 62 in the housing 64 for sampling chamber 66. Pitot tube 34 acts as a source of sampled gas, which gas travels into the opening 40 of the tube 34, through the portions 38, 44, 52, 48 and 56 and to the sampling chamber 66.

The second flow tube 32 includes a section 42 extending into the flow passage 26. Section 42 terminates in outlet 36, where the wall of tube 32 forms a planar peripheral face 37 around the outlet 36. The planar peripheral face 37 is at an angle of less than ninety degrees to the flow direction 18 and to the axis of section 42 of tube 32. The tip 39 of the tube 32 shields the outlet 36 from the oncoming flow of gas and the shape of the opening 36 provides a low pressure return for the exhaust gas, drawing the gas out of the sampling chamber 66 back into the passage 26.

Section 42 extends through a hole through the plug 30, where section 50 rises out of the plug 30 exterior of the converter 10. A bend 46 of approximately 90 degrees leads to section 54 of tube 32, which is parallel to the flow axis of exhaust gas through the converter 10. Section 54 terminates in opening 60 of housing 64 for sampling chamber 66.

The plug 30 is sealingly engaged around the portions of tubes 32 and 34 that pass through the plug 30. Additionally, tubes 32 and 34 are sealingly engaged in openings 60 and 62 of housing 64.

When the apparatus 28 is mounted to a flow passage, such as when plug 30 is mounted to the shell 12 as shown, and a flow of gas passes through the flow passage 26, a constant sample of the gas flow is cycled through the pitot tube 34 to the sampling chamber 66 and from the sampling chamber 66 through the return tube 32 back into the flow passage 26. The flow through the tubes 34 and 32 and sampling chamber 66 provides a constant sample of the gas flowing through passage 26 to the sampling chamber 66.

The sampling chamber 66 is defined by housing 64 that, in the example shown, is circular cylindrical in shape with a closed end 73 and an open end 72 opposite the closed end 73. The open end 72 in this example has thicker walls 70 defining a threaded opening 68 for threadably engaging a threaded housing portion 74 on oxygen sensor 71 of a known type. Through threaded portion 74, the sensor 71 sealingly engages the end 72 of the housing 64 and maintains the oxygen sensor 71 in place, exposing the sensor's sensing chamber 76 to the sample of exhaust gases flowing through sampling chamber 66. In this manner, the sensor 71 is exposed to variations in the oxygen content of the exhaust gas within flow passage 26 without requiring the sensor 71 to have its sensing chamber 76 within the flow passage 26 and without requiring the sensor 71 to itself pass through the walls of the catalytic converter 10 or other flow passage.

An advantage provided by the structure shown herein is that the sensor 71, flow tubes 32 and 34 and plug 30 can be packaged in a single unit and easily implemented into a wide variety of flow passages containing gases to be sensed. In contrast to certain prior art systems in which sampling chambers have an inlet tube receiving gas at one point in the flow stream and an outlet tube returning gas at a point downstream from where the inlet tube is located, the structure shown in FIGS. 1 and 2 has the inlet and outlet tubes positioned in approximately the same point in the exhaust gas flow. In the example shown, the outlet tube extends through the plug 30 upstream of where the inlet tube extends through the plug. While the prior art takes advantage of the pressure difference between the upstream and downstream points where the inlet and outlet tubes are located, this invention uses the shape of the flow tubes 34 and 32 and the shape of inlet 40 and outlet 36 to create a pressure difference across inlet 40 and outlet 36, forcing gas through the tubes 32 and 34 and sampling chamber 66. This advantageous configuration of the flow tubes 32 and 34 allows the tubes to enter the flow chamber at the same point through the single solid plug 30 shown.

Figure 3:
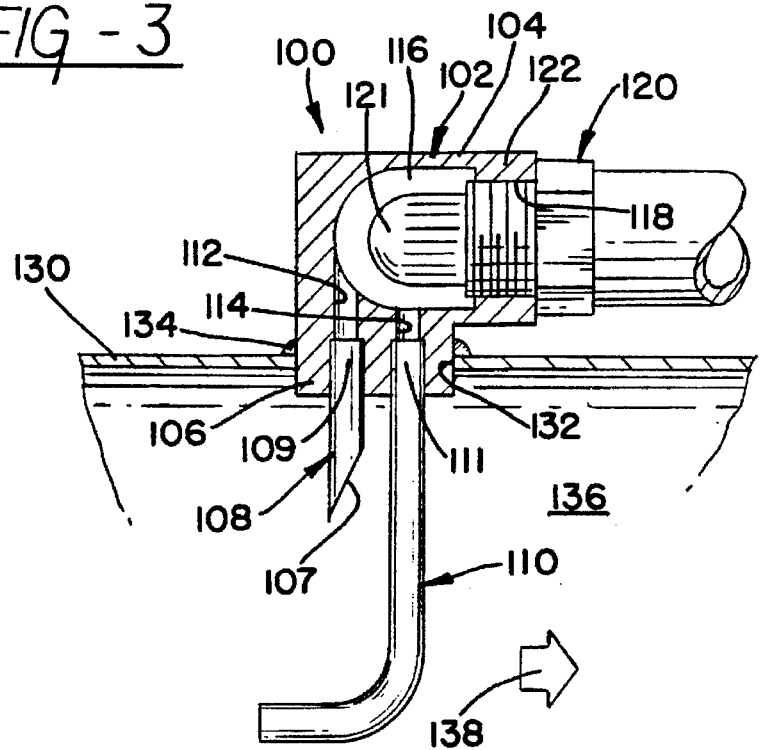
FIGS. 3 and 4 illustrate a second example according to this invention.
Figure 4:
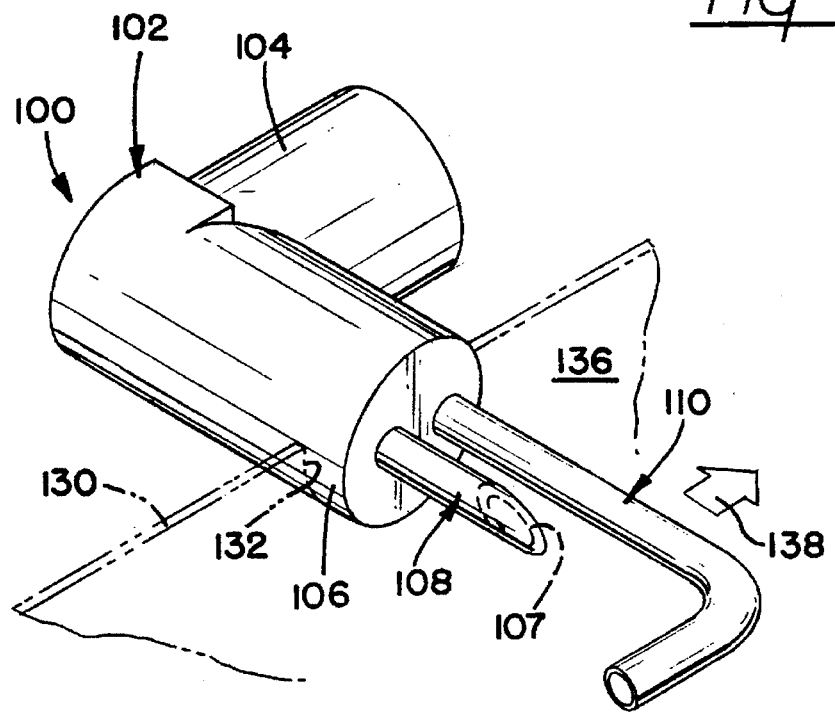

In the example shown in FIGS. 1 and 2, solid plug 30 is space separated from the housing 64 and comprises a separate part of the structure. Referring now to FIGS. 3 and 4, an example apparatus for sensing exhaust gas according to this invention is shown in which the plug and the housing of the sampling chamber are integral.

Exhaust gas flows through the flow passage 136 in the direction of arrow 138. Flow passage 136 has an outer wall 130, in which an opening 132 is provided into which the example apparatus for sensing exhaust gas 100, according to this invention, is sealingly mounted. The apparatus 100 includes a housing 102 having integrally formed therein a plug 106 that fits within the opening 132 and is sealingly affixed therein by a weld 134 surrounding the entire circular periphery of the plug 106.

Within the flow passage 136, pitot tube 110 provides pressure intake of a sample of the gas flowing through passage 136, through tube 110 and into the sampling chamber 116. Tube 110 has its top end 111 tightly and sealingly mounted within and terminating in the plug section 106 of the housing 102. Above the end 111, flow passage 114 provides a path for gas flow from the end 111 of pitot tube 110 to the sampling chamber 116, where the sensing element 121 of sensor 120 is located. The second tube 108 has an open end 107 with its peripheral face at an angle of less than 90 degrees to the axis of tube 108 providing an outlet of gas from the tube 108 into the flow passage 136 generally aligned with the direction of gas flow indicated by arrow 138.

End 109 of tube 108 terminates sealingly in the plug section 106 of the housing 102. Above end 109, a passage 112 leads from sampling chamber 116 through housing 102 to tube 108 so that gas that flows into the sampling chamber from tube 110 is drawn through the passage 112 to the tube 108 and through the tube 108 back to the flow passage 136. This structure continuously cycles a sample of the gas from passage 136 through the sampling chamber 116 and exposes the sensing element 121 of sensor 120 to a continuously updated sample of exhaust gas.

Housing 102 has a portion 104 defining the sampling chamber 116 and an open end 122 having a threaded opening 118 therein that engages a threaded portion of sensor 120 to firmly maintain the sensor 120 to the housing 102. The threaded engagement between the sensor 120 and the housing 102 seals the sensor 120 to the housing 102, closing the sampling chamber 116 from the outside atmosphere.

Both examples described above achieve the advantage of mounting the oxygen sensor parallel to the flow of exhaust gas, which prevents the necessity of the exhaust oxygen sensor projecting out of the wall of the flow passage and reduces the amount of space radial from the center of the flow passage or catalytic converter that is required by the sensor 120 or 71.

Figure 5:
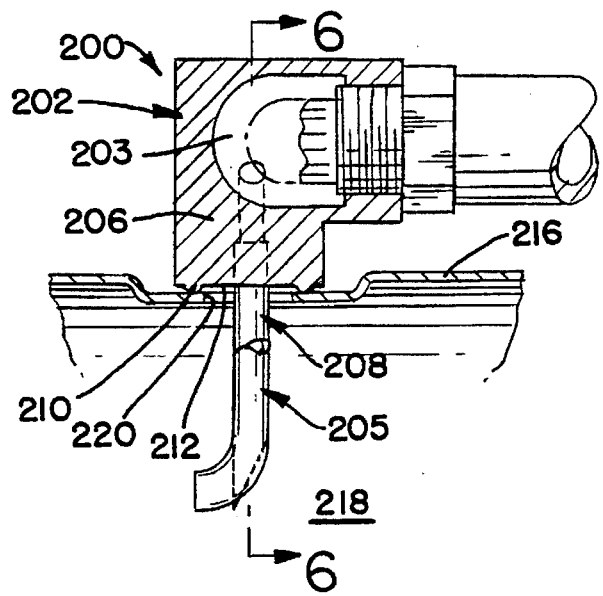
FIGS. 5, 6 and 7 illustrate a third example according to this invention.
Figure 6:
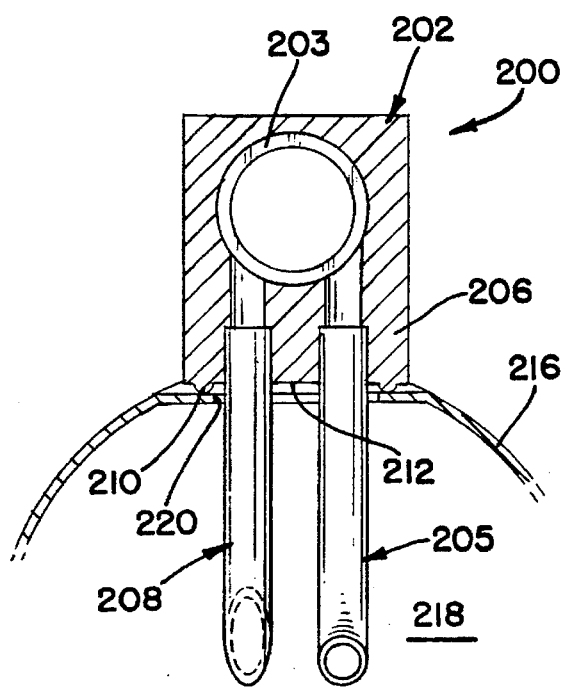
Figure 7:
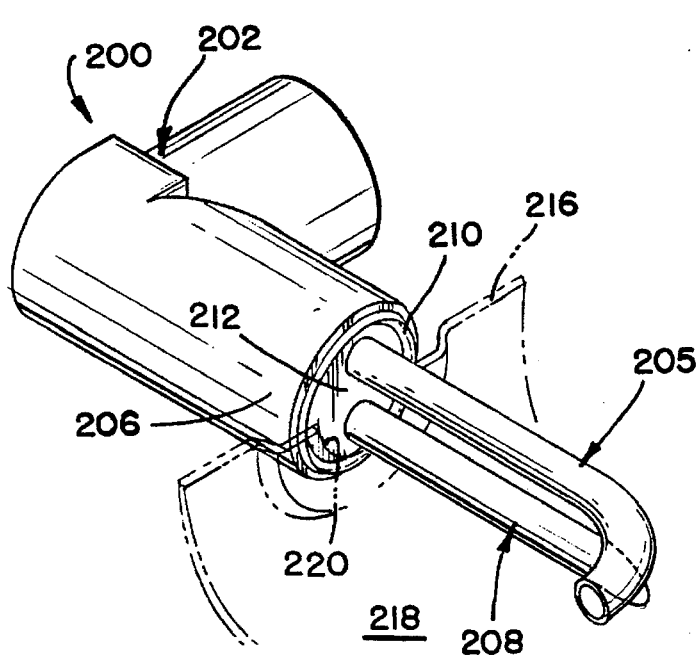

Referring now to FIGS. 5, 6 and 7, the example apparatus for sensing exhaust gas 200 shown is similar to the apparatus shown in FIGS. 3–4. The housing 202 defines the sampling chamber 203 and passages that lead to pitot tube 205 and outlet tube 208. In this example, the pitot and outlet tubes 205 and 208 are arranged laterally in a plane perpendicular to the air flow through the passage 218 to which the sensor is mounted. The housing includes plug portion 206 having end 212 to which the pitot and outlet tubes 205 and 208 engage in a manner similar to the example in FIGS. 3 and 4.

In this example, the end 212 includes an annular rib 210 extending along the periphery of the end 212 and projecting in the direction of the tubes 205 and 208. This rib 210 allows the housing 202 to be projection welded to the wall 216 of the passage to which the sensor is mounted. For example, the rib is placed against the passage wall 216 with the tubes 205 and 208 extending through an opening 220 in the passage. Then an electric current is passed briefly through the body 202 and rib 210 to the wall 216 of the passage 218. This current causes the rib 210 to melt along with a small portion of the metal of the wall 216. When the current is terminated, the metal solidifies, and the housing 202 is welded in place on the passage wall 216.

For small diameter pipe implementations, it may be desirable to fabricate end 212 of the housing 202 with an arch. This allows a sealing engagement with the wall of the pipe without having to flatten the pipe wall at the point of the projection weld.

One skilled in the art will recognize that the apparatus for sensing exhaust gas according to this invention provides a universal type system and can be mounted to virtually any exhaust flow passage in which it is desirable to sense exhaust gas. Example mounting locations include an exhaust manifold on an engine, an exhaust manifold down pipe or another pre-converter or post-converter pipe. The apparatus can be mounted within the catalytic converter, for example, as shown in FIG. 1, between the monoliths, or alternatively, upstream of the monoliths or downstream of the monoliths, depending on the system and where in the system it is desirable to measure the exhaust gas oxygen content.

In many systems, it may be desirable to mount more than one sensor using the apparatus for sensing exhaust gas according to this invention and thus, a plurality of such apparatuses will be used in the system.

We claim:

1. An apparatus for sensing exhaust gas comprising: first and second tubular passages; a solid plug through which the first and second tubular passages pass and to which the tubular passages are sealingly engaged; a sampling chamber mounted to and in flow contact with the first and second tubular passages, wherein the first tubular passage provides gas flow into the sampling chamber and the second tubular passage takes gas flow out of the sampling chamber; and a flow passage having a tubular wall with an opening therein to which the solid plug is sealingly engaged, wherein the first and second tubular passages extend from inside the flow passage, through the plug, to the sampling chamber mounted outside of the flow passage, wherein the solid plug comprises part of a housing for the sampling chamber.

2. An apparatus for sensing exhaust gas according to claim 1, wherein the flow passages is a catalytic converter and wherein, within the catalytic converter, the first and second tubular passages are located between first and second converter monoliths.

* * * * *